(12) United States Patent
Penner et al.

(10) Patent No.: US 7,678,087 B2
(45) Date of Patent: Mar. 16, 2010

(54) EQUINE INTRANASAL DELIVERY SYSTEM

(75) Inventors: Steven J. Penner, Broomfield, CO (US); Randal W. Sebring, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 1522 days.

(21) Appl. No.: 10/941,727

(22) Filed: Sep. 15, 2004

(65) Prior Publication Data

US 2005/0039739 A1 Feb. 24, 2005

Related U.S. Application Data

(63) Continuation of application No. 10/089,244, filed as application No. PCT/US00/26870 on Sep. 29, 2000, now Pat. No. 6,686,343, which is a continuation of application No. 09/408,548, filed on Sep. 29, 1999.

(51) Int. Cl.
*A61M 31/00* (2006.01)
(52) U.S. Cl. ..................................... 604/275
(58) Field of Classification Search .............. 604/239, 604/240–243, 310, 275
See application file for complete search history.

(56) References Cited

U.S. PATENT DOCUMENTS

| 3,874,083 A * | 4/1975 | Buckley ........................ 433/80 |
| 3,927,208 A | 12/1975 | Zygraich et al. ............... 424/89 |
| 3,950,512 A | 4/1976 | Emery et al. ................... 424/89 |

(Continued)

FOREIGN PATENT DOCUMENTS

EP 0444905 A1 2/1991

(Continued)

OTHER PUBLICATIONS

Anderson, E., et al., "Evaluation of a Cold-Adapted Influenza B/Texas/84 Reasserting Virus (CRB-87) Vaccine in Young Children", Journal of Clinical Microbiology, Sep. 1992, p. 2230-2234.

(Continued)

*Primary Examiner*—Manuel A Mendez
(74) *Attorney, Agent, or Firm*—CR Miles, PC; Craig R. Miles

(57) ABSTRACT

This invention relates to apparatus and methods of delivering various compositions including medicaments to a variety of targets. The invention includes a dose administrator (1) which may be used for intranasal delivery of compositions or medicaments, such as live virus vaccines, to both humans and animals. An axial collapse prevention element (2) to prevent excessive axial deflection of the dose administrator (1) or a dose-location coordinate indicator (3) to facilitate the delivery of a dose to the desired target location may be coupled to the dose administrator (1). An intranasal probe (4) having a force dissemination contact surface (7) may be responsive to a first end of the dose administrator (1). The dose may be delivered from a conformable dose sequestration element (10) through an aperture which penetrates the dose delivery aperture element (5) and the dose may be caused to stream by coupling a stream delivery element (6) to the dose delivery aperture element (5). The force application element (12) which acts upon the dose may be separated from the dose by a fluid dose propellant (13). While the invention may be used for numerous applications, it specifically addresses the difficulties of delivering cold-adapted live equine influenza viruses intranasally to equids.

26 Claims, 11 Drawing Sheets

U.S. PATENT DOCUMENTS

| | | | | |
|---|---|---|---|---|
| 3,953,592 | A | 4/1976 | PEetermans | 424/89 |
| 3,962,422 | A | 6/1976 | Parks | 424/89 |
| 4,009,258 | A | 2/1977 | Kilbourne | 424/89 |
| 4,029,763 | A | 6/1977 | Kilbourne | 424/89 |
| 4,053,583 | A | 10/1977 | Gits et al. | 424/90 |
| 4,110,427 | A | 8/1978 | Kalat | 424/46 |
| 4,110,433 | A | 8/1978 | Purdy, III | 424/89 |
| 4,132,775 | A | 1/1979 | Volenec et al. | 424/89 |
| 4,136,168 | A | 1/1979 | Fontanges | 424/89 |
| 4,195,076 | A | 3/1980 | Fontanges | 424/43 |
| 4,512,972 | A | 4/1985 | Schmidt-Ruppin | 424/89 |
| 4,554,158 | A | 11/1985 | Russell | 424/89 |
| 4,554,159 | A | 11/1985 | Roizman et al. | 424/89 |
| 4,613,500 | A | 9/1986 | Sukuki et al. | 429/85 |
| 4,683,137 | A | 7/1987 | Coggins et al. | 424/89 |
| 4,693,893 | A | 9/1987 | Campbell | 424/89 |
| 4,767,416 | A * | 8/1988 | Wolf et al. | 604/239 |
| 4,800,078 | A | 1/1989 | Prince et al. | 424/86 |
| 4,962,091 | A | 10/1990 | Eppstein et al. | 514/2 |
| 4,990,140 | A * | 2/1991 | Black | 604/192 |
| 5,053,022 | A | 10/1991 | Bryant et al. | |
| 5,158,761 | A | 10/1992 | Kamishita et al. | 424/45 |
| 5,215,739 | A | 6/1993 | Kamishita et al. | 424/45 |
| 5,250,298 | A | 10/1993 | Gelb, Jr. | 424/89 |
| 5,427,782 | A | 6/1995 | Compans et al. | 424/192.1 |
| 5,484,406 | A * | 1/1996 | Wong et al. | 604/87 |
| 5,579,758 | A * | 12/1996 | Century | 128/200.22 |
| 5,601,077 | A | 2/1997 | Imbert | 128/200.14 |
| 5,720,762 | A | 2/1998 | Bass | 606/192 |
| 5,843,451 | A | 12/1998 | Compans et al. | 424/192.1 |
| 6,716,190 | B1 * | 4/2004 | Glines et al. | 604/70 |

FOREIGN PATENT DOCUMENTS

| | | |
|---|---|---|
| EP | 0444905 B1 | 2/1991 |

OTHER PUBLICATIONS

Belshe, R., et al., "Immunization of Infants and Young Children with Live Attenuated Trivalent Cold-Recombinant Influenza A H1N1, H3N2, and B Vaccine", The Journal of Infectious Diseases, 1992, p. 727-732.

Brown, A. and Slusser, J., "Propellant-driven Aerosols of Functional Proteins as Potential Therapeutic Agents in the Respiratory Tract", Immunopharmacology, 28, 1994, p. 241-257.

Chanock, Robert M., et al, "Viral Immunology and Immunopathology", Current Approaches to Viral Inununoprophylaxis, Academic Press, New York, 1975, p. 291-316.

Chien, Y.W., et al., "Nasal Systemic Drug Delivery", Anatomy and Physiology of the Nose, Chapter 1, p. 1-26, 1989.

Dolovich, M., "Physical Principles Underlying Aerosol Therapy", Journal of Aerosol Medicine, vol. 2, No. 2, 1989, p. 171-186.

Exhibit A, Wolfe Tory Medical, Inc., 79 West 4500 South, Salt Lake City, Utah 84107, Date received 1999.

Exhibit B, Fort Dodge Animal Health, Overland Park, Kansas, Date received 1998.

Exhibit C, Pfizer Animal Health, 601 West Cornhusker Highway, Lincoln, Nebraska, Date received 1999.

Exhibit D, Trade Secret/Confidential Information.

Genesis Industries, Inc. brochure, "Select Innovative Versatile Quality delivery Systems and Syringe Components", 1995, four pages.

Haneberg, B., et al, "Intranasal Administration of Meningococcal Outer Membrane Vesicle Vaccine Induces Persistent Local Mucosal Antibodies and Serum Antibodies with Strong Bactericidal Activity in Humans, Infection and Immunity", 66(4), p. 1334-1341, Apr. 1998.

Hannant, D. and Mumford, J., "Cell Mediated Immune Responses in Ponies Following Infection with Equine Influenza Virus (H3N8): the Influence of Induction Culture Conditions on the Properties of Cytotoxic Effector Cells", Veterinary Immunology and Immunopathology, 21, 1989, p. 327-337.

Hannant, D., et al., "Duration of Circulating Antibody and Immunity Following Infection with Equine Influenza Virus", The Veterinary Record, Feb. 6, 1988, two pages.

Henry, R.J., et al, "A pharmacokinetic Study of Midazolam in Dogs: Nasal Drop Versus Atomizer Administration", Journal of the American Academy of Pediatric Dentistry, 20:5, p. 321-326, 1998.

Heska brochure, "Finally, A Vaccine Proven To Protect Against Equine Influenza" 10 Pages.

Hoffert, S., "Biotech Innovations Aim to Conquer Influenza Virus", The Scientist, Mar. 2, 1998, p. 1 and 6.

Holmes, D., et al., "Live Temperature Sensitive Equine-2 Influenza A Virus Vaccine: Production and Efficiency in Experimental Ponies", Equine Infectious Diseases VI, 1992 p. 253-258.

Jing-Quing, W., et al., "An Experimental Study on Nasal Absorption of Gentamycin in Dogs", Chinese Medical Journal, 107(3), p. 219-221, 1994.

Keitel, W., et al., "Trivalent Attenuated Cold-Adapted Influenza Virus Vaccine: Reduced Viral Shedding and Serum Antibody Responses in Susceptible Adults", The Journal of Infectious Diseases, 1993, p. 305-311.

Klaus-Dieter-Budras, "Anatomy of the Horse, an Illustrated Text", 2nd Edition, Mosby-Wolfe, London, 1994.

Louon, A., et al., "Sedation with Nasal Ketamine and Midazolam for Cryotherapy in Retinopathy of Prematurity", British Journal of Ophthalmology, 77(8). p. 529-530, 1993.

Maassab, H.F., "Biologic and Immunologic Characteristics of Cold-Adapted Influenza Virus", Journal of Immunology 102, No. 3, p. 728-732, 1969.

Maassab, H.F., et al, "Development and Characterization of Cold-Adapted Viruses for Use As Live Virus Vaccines", Vaccine Department of Epidemiology, School of Public Health, The University of Michigan vol. 3, 1985.

Mumford, et al, "Serological Methods for Identification of Slowly-Growing Herpes viruses Isolated from the Respiratory Tract of Horses", Equine Infectious Disease IV, The Journal of Equine Medicine and Surgery, Supplement No. I, 1978, p. 49-52.

Mumford, et al, "WHO/OIE Meeting: Consultation on Newly Emerging Strains of Equine Influenza", Vaccine 11, p. 1172-1174, 1993.

Mumford, et al, "Studies on Picornaviruses Isolated from the Respiratory Tract of Horses", Equine Infectious Disease IV, The Journal of Equine Medicine and Surgery, Supplement No. I, 1978, p. 421-429.

Nelson, K., et al., "Local and Systemic Isotope-Specific Antibody Responses to Equine Influenza Virus Infection Versus Conventional Vaccination", Vaccine 1998, vol. 16, No. 13, pp. 1306-1313.

Newman, S.P., et al, "CHEST, In Vitro Comparison of DeVilbiss Jet and Ultrasonic Nebulizers", 1987, 92: 991-994.

Nott, M.R., et al., "Topical Anesthesia for the Insertion of Nasogastric Tubes", European Journal of Anesthesiology, 12(3), 1995.

PCT Application, PCT/US00/26,870, entitled, "Intranasal Delivery System", filed Sep. 29, 2000.

Penner, et al., Veterinary Concepts® catalog, Oct. 9, 1996, 116 pages.

Ralley, F.E., "Intranasal Opiates: Old Route for New Drugs", Canadian Journal of Anesthesia, 36(5) 491-493, 1989.

Thomas, S.H., et al, "Variability in the Measurement of Nebulized Aerosol Deposition in Man", Clinical Science 1991: 81: 767-775.

Tomoda, T., et al., "Prevention of Influenza by the Intranasal Administration of Cold-Recombinant, Live-Attenuated Influenza Virus Vaccine: Importance of Interferon-γ Production and Local IgA Response", Vaccine, vol. 13, No. 2, 1995, pp. 185-190.

U.S. Appl. No. 09/133,921, entitled, "Cold-Adapted Equine Influenza Viruses Field of the Invention".

Value Plastics Web Page Site, www.valueplastics.com, downloaded Jun. 10, 1998.

Vincent, J., "The Fate of Inhaled Aerosols: A Review of Observed Trends and Some Generalizations", British Occupational Hygiene Society, vol. 34, No. 6, 1990, pp. 623-635.

Wagner, B, et al, "A Double-Blind, Placebo-Controlled Evaluation of Intranasal Metoclopramide in the Prevention of Postoperative Nausea and Vomiting", Pharmacotherapy, 16(6), 1063-1069 1996.

Wolfe Tory Medical, Inc. web site, www.wolfetory.com, downloaded Jul. 20, 1999, 7 pages.

Wolfe Tory Medical, Inc. web site, www.wolfetory.com, downloaded Sep. 20, 1999, 6 pages.

Wolfe, T., "Intranasal Medication Administration: Literature Review", www.wolfetory.com/intra.html, downloaded Sep. 20, 1999, 17 pages.

Youngner, J., et al., "Effect of Simultaneous Administration of Cold-Adapted and Wild-Type Influenza A Viruses on Experimental Wild-Type Influenza Infection in Humans", Journal of Clinical Microbiology, Mar. 1994, vol. 32, No. 3, pp. 750-754.

* cited by examiner

Section A-A

Section B-B

Section C-C

EQUINE INTRANASAL DELIVERY SYSTEM

This United States continuation application claims priority to U.S. patent application Ser. No. 10/089,244, filed Mar. 27, 2002, which was the United States National Stage of International Patent Application No. PCT/US00/26870, filed Sep. 29, 2000, which was a continuation of U.S. patent application Ser. No. 09/408,584, filed Sep. 29, 1999, now issued as U.S. Pat. No. 6,398,774, each hereby incorporated by reference herein.

I. TECHNICAL FIELD

This invention relates to an equine intranasal delivery system for the delivery of cold-adapted equine viruses. The invention also includes both apparatus and methods for the intranasal delivery of various materials, compositions or medicaments to both humans and animals. Generally, the invention provides basic technology for the delivery of various compositions to target locations.

II. BACKGROUND

There are many advantages to intranasal administration of medications and other compositions which include, among others, a direct route to the blood stream, avoidance of hepatic first pass metabolism, bioavailability, ease and convenience, and proximity to the central nervous system. See Y. W. Chien et al., *Anatomy and Physiology of the Nose*, Nasal Systemic Drug Delivery, Chapter 1, 1-26, 1989. Various types of compositions, therapeutics, prophylactics or otherwise, may be delivered intranasally including, but not limited to, topical anesthetics, sedatives, hypnotics, analgesics, ketamines, opiates, glucagons, vaccines, anti-nausea and motion sickness medications, antihistamines, antihypertensive drugs, psychoactive medications, antibiotics, and hormones. See, as examples, M. R. Nott et al., *Topical Anaesthesia for the Insertion of Nasogastric Tubes*, European Journal of Anaesthesiology, 12(3), May 1995; R. J. Henry et al, *A pharmacokinetic Study of Midazolam in Dogs: Nasal Drop Versus Atomizer Administration*, Journal of the American Academy of Pediatric Dentistry, 20(5), 321-326, 1998; J. Lithander et al., *Sedation with nasal Ketamine and Midazolam for Cryotherapy in Retinopathy of Prematurity*, British Journal of Ophthalmology, 77(8), 529-530, 1993; F. E. Ralley, *Intranasal Opiates: Old Route For New Drugs*, Canadian Journal of Anesthesiology, 36(5) 491-493, 1989; B. Haneberg et al, *Intranasal Administration of Mengiococcal outer membrane vesicle vaccine induces persistent local Mucosal Antibodies and Serum Antibodies with Strong Bactericidal Activity in Humans*, Infection and Immunity, 66(4), 1334-1341, 1998; B. K. Wager et al, *A Double Blind Placebo-Controlled Evaluation of Intranasal Metoclopramide in the Prevention of Postoperative nausea and Vomiting*, Pharmacotherapy, 16(6), 1063-1069 1996; and J. Q. Wang, et. al., *An Experimental Study on Nasal Absorption of Gentamycin in Dogs*, Chinese Medical Journal, 107(3), 219-221, 1994.

Specifically with respect to live virus vaccines, it has been shown that they are often too pathogenic for use as immunogens for either humans or animals as described in U.S. Pat. No. 3,953,592. Attempts to vaccinate against viral infection with inactivated virus, however, may not offer effective protection and can produce undesirable side effects as indicated in U.S. Pat. No. 3,953,592; R. Belshe et al, *Immunization of Infants and Young Children with Live Attenuated Trivalent Cold-Recombinant Influenza A H1N1, H3N2, and B Vaccine*, The Journal of Infectious Disease, Volume 165, 727-732, 1992; K. M. Nelson et al., *Local and Systemic Isotype-specific Antibody Responses to Equine Influenza Virus Infection Versus Conventional Vaccination*, Vaccine, Volume 16, Number 13, 1998. Injection of equids with inactivated viruses may cause, for example, inflammatory reactions at the site of injection. See Mumford et al., *Serological Methods for Identification of Slowly-Growing Herpesviruses Isolated from the Respiratory Tract of Horses*, Equine Infectious Disease IV, 49-52, 1978; Mumford et al., *Consultation on Newly Emerging Strains of Equine Influenza*, Vaccine 11, 1172-1174, 1993. It has also been shown that protective responses to viral infection are not limited to the production of antibodies but that a local antibody system and an interferon production mechanism operate at the primary site of infection in the nasal passage membranes as disclosed by U.S. Pat. No. 4,132,775; T. Tomoda et al., *Prevention of Influenza by the Intranasal Administration of Cold-Recombinant, Live-attenuated Influenza Virus Vaccine: Importance of interferon-γ Production and Local IgA Response*, Vaccine, Volume 13, Number 2, 185-190, 1995; and Holmes, Lamb, Coggins, et al, *Live Temperature Sensitive Equine-2 Influenza A Virus Vaccine: Production and Eficacy in Experimental Ponies*, Equine infectious disease VI, 253-258, 1992.

As such, intranasal delivery of the above mentioned compositions has become a preferred route of administration for both inactivated viruses as described by U.S. Pat. No. 3,953,592, and cold-adapted live virus vaccines which are inhibited from replication in the range of the normal body temperature but do replicate at lower temperatures, such as perhaps, associated with the mucosae of the upper respiratory tract as disclosed by U.S. Pat. No. 3,927,208; Maassab, et al., *Biologic and Immunologic Characteristics of Cold-Adapted Influenza Virus*, Journal of Immunology. 102, 728-732, 1969; and Keitel et al., *Trivalent Attenuated Cold-Adapted Virus Vaccine: Reduced Viral Shedding and Serum Antibody Responses in Susceptible Adults*, The Journal of Infectious Disease, Volume 167, 305-311, 1993. Intranasal delivery of compositions has also been effective for certain reassortant cold-adapted viruses which may also possess a dominant interference phenotype which may inhibit the growth of the corresponding wild-type strains and other heterologous viruses as disclosed by U.S. Pat. Nos. 4,683,137 and 4,693,893.

Due to the increased use of intranasal delivery of various compositions, including inactivated and cold-adapted live viruses, in both humans and animals, there is corresponding demand in the marketplace for intranasal apparatus and methods of intranasal delivery which address existing problems, and which are especially acute with respect to equids including, for example, horses, ponies, or exotic equids such as zebra which may be part of a zoological collection, or otherwise.

A significant problem with intranasal delivery of compositions is interspecies and intraspecies anatomical variation. With regard to one aspect of these differences, it is evident from casual observation that the gross morphology of bovine species present a shorter nasal passage then, for example, equid species. An inflexible intranasal administrator, for example, may be adequate for intranasal delivery of a composition or dose to a bovine where the intranasal administrator need only tranverse a short distance in the bovine nasal passage, however, such an inflexible device may not be suitable for equids where the intranasal administrator may have to traverse several inches within the nasal passages of an equid.

A related problem with intranasal delivery of compositions in equids as opposed to bovine, for example, is the presence of a false nostril (nasal diverticulum) as described by Klaus, Dieter, Budras, *Anatomy of the Horse an Illustrated Text,* 2nd edition, Mosby-Wolfe, London, 1994. The nasal diverticulum presents two problems with regard to intranasal delivery in equids although other species may have anatomical structures which present equivalent difficulties. First, an intranasal probe for equids must be designed such that the user has an immediate means of determining if the delivery aperture of the intranasal probe has properly entered the nasal passage or if the intranasal probe has inadvertently entered the nasal diverticulum. The second problem associated with the nasal diverticulum is that the type of cells which line the nasal diverticulum are not the same type of cells which line the nasal passage of the upper respiratory tract. Delivery of compositions, including the delivery of cold-adapted live viruses, to the type of cells which line the nasal diverticulum may not provide therapy because such cells may not be susceptible to such compositions, or cold adapted live viruses. While the nasal diverticulum provides a remarkable example of the necessity of coordinating therapeutic compositions with an anatomical location having cells susceptible to a particular composition or dose, dose-location coordination may be an important aspect of intranasal delivery in many other species.

Another significant problem with intranasal delivery is the movement and regional distribution of the composition or dose subsequent to administration. The deposition of a composition or dose after intranasal delivery depends upon particle inertia, sedimentation due to gravity, and diffusion due to Brownian motion. M. Dolovich, *Principles Underlying Aerosol Therapy*, Journal of Aerosol Medicine, Vol. 2, No. 2, 1989; see also A. Brown and J. Slusser, *Propellent-driven Aerosols of Function Proteins as Potential Therapeutic Agents in the Respiratory Tract*, Immunopharmacology 28, 241-257, 1994. Each of these mechanisms can be dependent upon the particle size of the dose or composition delivered. As disclosed by M. Dolovich, particles having a diameter of less than about 1 micrometer can remain suspended as the time required for the particle to diffuse to an airway wall tends to be greater than the time to complete the inspiratory phase of a normal breath. Optimum deposition in the lung may be achieved with particles having a diameter of about 3 micrometers. Larger particles having a diameter of greater than about 5 micrometers are often deposited in the upper airways. M. Dolovich, at pages 173-174. As such the proper particle size should be selected depending on where in the airway or lung compartment deposition is to occur. With respect to cold-adapted viruses delivered intranasally from devices designed to provide a fine aerosol or heterodisperse aerosol, a portion of the dose may remain suspended in the respired air and subsequently exhaled without deposition. This may be particularly true when treating animals which may not be instructed to hold their breath. Alternately, the cold-adapted virus having a somewhat larger particle size may remain suspended and then deposited in the lung compartment. Once in the lung compartment the virus may be prohibited from replication by exposure to the normal body temperature of the animal. In either event, a portion of the dose may be rendered ineffective because the dose was delivered as a particle of non-optimal size.

To the extent that "multiple studies show that atomized pump is the best nasal delivery system because it gives a constant dose and a very good mucosal distribution" and that research has demonstrated "clearance of spray is much slower than clearance of drops", these studies, research and marketing descriptions, teach away from a non-aerosol-location coordinated intranasal delivery system. See T. Wolfe, *Intranasal Medication Administration: Literature Review*, Wolf Tory Medical, Incorporated, http://www.wolfetory.com/intr.html, 1-17, at page 3, 1999.

A related problem is coordinating the delivery of a particular type of composition with a particular location of delivery. Often the location to which the dose is to be administered is hidden from view. As such, there may be little assurance that the composition has actually been delivered to the proper location or target. This may be particularly problematic for those individuals that have little or no formal medical training.

Yet another problem with existing devices for intranasal administration of compounds is generation of excess physical stimulation of the nasal passage as the intranasal probe or dose administrator is guided along the intranasal passage. This physical stimulation may be more acute when the force used to move the intranasal probe along the intranasal passage is translated to a tip of the dose administrator having a small surface area which contacts the nasal mucosae. As can be understood, an intranasal administrator comprising a relatively small diameter tube with a thin sidewall may be more likely to irritate, cut, score or pierce the intranasal surface causing the human or animal to move unpredictably. After the intranasal passage has been injured it may also subsequently become infected and require additional medical attention. Moreover, when attempting to administer a composition or dose intranasally to a human or an animal, unpredicted movement caused by such physical stimulation may force the intranasal dose administrator into contact with the eye or perhaps into contact with the person attempting to administer the composition or dose. This inadvertant movement may also transfer biological fluids between the patient and the practitioner or cause the loss of a portion or all of the composition or dose. As such, reducing physical stimulation of the spot contacted by the intranasal probe may be preferred.

Another problem related to intranasal administrators which have a small diameter or thin wall construction is that axial deflection of the intranasal administrator may be excessive under the typical forces encountered during use. Axial collapse of the administrator may result in a failure to deliver the dose properly, additional physical stimulation of the intranasal passage, or cause injury.

Still another significant problem is the amount of composition or dose that may remain in devices upon delivery of the composition or dose to the patient. This "dead volume" within the device represents an amount of the dose or composition that is unavailable to the patient. With regard to some types of jet nebulizers, this may amount to as much as 0.5-1.0 milliliters of concentrated solution, as disclosed by M. Dolovich, *Physical Principles Underlying Aerosol Therapy*, Journal of Aerosol Medicine, Volume 2, Number 2, 1989. The dead volume associated with intranasal devices having administrators or intranasal probes designed for equids, for example, which are quite long may have a similarly large dead volume. Even if devices with a smaller dead volume were designed, even such smaller volume of a composition or a dose made unavailable to the patient may be significant where the cost of the dose is high. An intranasal delivery system which reduces dead volume by design of the intranasal device or by the method of use may provide substantial benefit.

Another problem with some delivery systems may be a lack of unitized construction. Components which may have been produced as a single unit may comprise several component parts which are compression fit together, or bonded together with use of a solvent, as can be understood from the Misty device. These several component parts may disassemble during intranasal administration or subsequently become lodged in the intranasal passage of the human or animal. These component parts may cause immediate injury or remain in the intranasal passages undiscovered to cause subsequent injury. Removal of these component parts from the intranasal passages may also require additional medical procedures.

From the consumer's point of view there are several problems which have not been adequately addressed by existing systems for the administration of compositions. The first is the fear of needles. Many people are needle phobic and as a result many people are not inoculated. S. Hoffert, *Biotech Innovations Aim to Conquer Influenza Virus*, The Scientist, 1 and 6, Mar. 2, 1998. A second problem for the consumer is the potential for inadvertent needle sticks which may transfer either the composition or physiological fluids from the patient to the person administering the composition or dose. A third problem for the consumer is proper disposal of needles. A delivery device which eliminates injection of the composition with a needle may induce the needle phobic to obtain inoculation and may also address the problems of inadvertent needle sticks and needle disposal. A fourth problem for the consumer untrained in medical or veterinary fields is the fear of self administration of compositions to themselves, or other humans or animals. A part of this fear may be the use of needles, or other devices, which the consumer believes may cause injury to the patient due to the consumer's lack of training. However, even with respect to delivery devices which may be designed for use without a needle, the consumer may have concerns that the composition or dose may be delivered in a manner that is not therapeutic for the patient. A properly engineered intranasal device may address these consumer concerns by providing features which assure proper measurement of a dose and delivery of the dose to an intranasal location in a manner which will be therapeutically effective.

As to each of these problems regarding devices for the delivery of compositions and the methods of delivering compositions, the present invention discloses technology which overcomes every one of the problems disclosed in a practical fashion.

III. DISCLOSURE OF THE INVENTION

Accordingly, the broad goal of the invention is to provide a delivery system for various compositions including medicaments which safely and effectively delivers the entire amount of a composition or a dose to the proper target. Specifically, the broad goal of the invention also addresses the particular requirements of intranasal delivery of such compositions and medicaments in the equine field which is particularly difficult due to the size, mobility and disposition of equids. The composition or dose delivery features disclosed are varied and may be incorporated into a variety of devices or used in numerous applications. Naturally, as a result of these several different and potentially independent aspects of the invention, the objects of the invention are quite varied.

One of the broad objects of the invention is to provide basic technology to improve the delivery of a wide variety of compositions, including medicaments, across a broad range of commercial, research, medical and veterinary applications.

Another object of the invention, is to provide specific apparatus and methods for the intranasal delivery of prophylactic and therapeutic compositions to both humans and animals incorporating the above mentioned basic technological aspects of the invention.

Another object of the invention is to define the scope of existing technology that may be improved by using such technology with specific strains of cold-adapted equine influenza virus.

Another object of the invention is to provide an intranasal delivery device for equids which specifically incorporates certain aspects of the invention so as to accommodate the longer or more complicated nasal passages of the equine anatomy.

Related to this object are certain embodiments of the invention which provide for the effective delivery of compositions or doses, including particular cold-adapted influenza or cold-adapted equine influenza viruses, to specific dose-location coordinates which may be hidden from visual observation. A particular goal is to provide apparatus and methods for assuring that specific strains of equine cold-adapted equine influenza viruses may be delivered to a location on the nasal mucosa of an equid having a temperature range suitable for replication of these specific equine influenza strains.

Another object of the invention is to provide an element which prevents the axial collapse of the dose administrator due to incidental contact as it is brought into position for delivery of the composition or dose to the target.

Another object of the invention is to provide delivery of the composition or dose in a manner which assures that a substantial portion of such composition or dose will remain in the proximity of the desired dose-location coordinate or target.

Another object of the invention is to minimize the cutting, scoring or other injuries and physical stimulation from the incidental contact of various surfaces, including intranasal passages, with the dose administrator as it is positioned for delivery of the composition or dose.

Another object of the invention is to minimize the amount of the dose which is retained by the dose delivery administrator after delivery of the composition or dose to the dose-location coordinate or target. Specifically, with respect to devices which have larger dead volumes or larger minimum dose delivery volumes, such as those which have longer dose administrators, this aspect of the invention allows the dose to be sequestered proximate to the dose delivery aperture. A sequestered dose come into contact with less surface area of the delivery system and is expelled from the dose administrator with a lower minimum delivery volume.

Another object of the invention is to make an uncomplicated delivery device which may be used by individuals that have little or no formal training. A goal related to this object is elimination of parts which may inadvertently become disassembled during the use of the device. Naturally further objects of the invention are disclosed throughout other areas of the specification and claims.

IV. BRIEF DESCRIPTION OF THE DRAWINGS

V. MODE(S) FOR CARRYING OUT THE INVENTION

Figure 1:
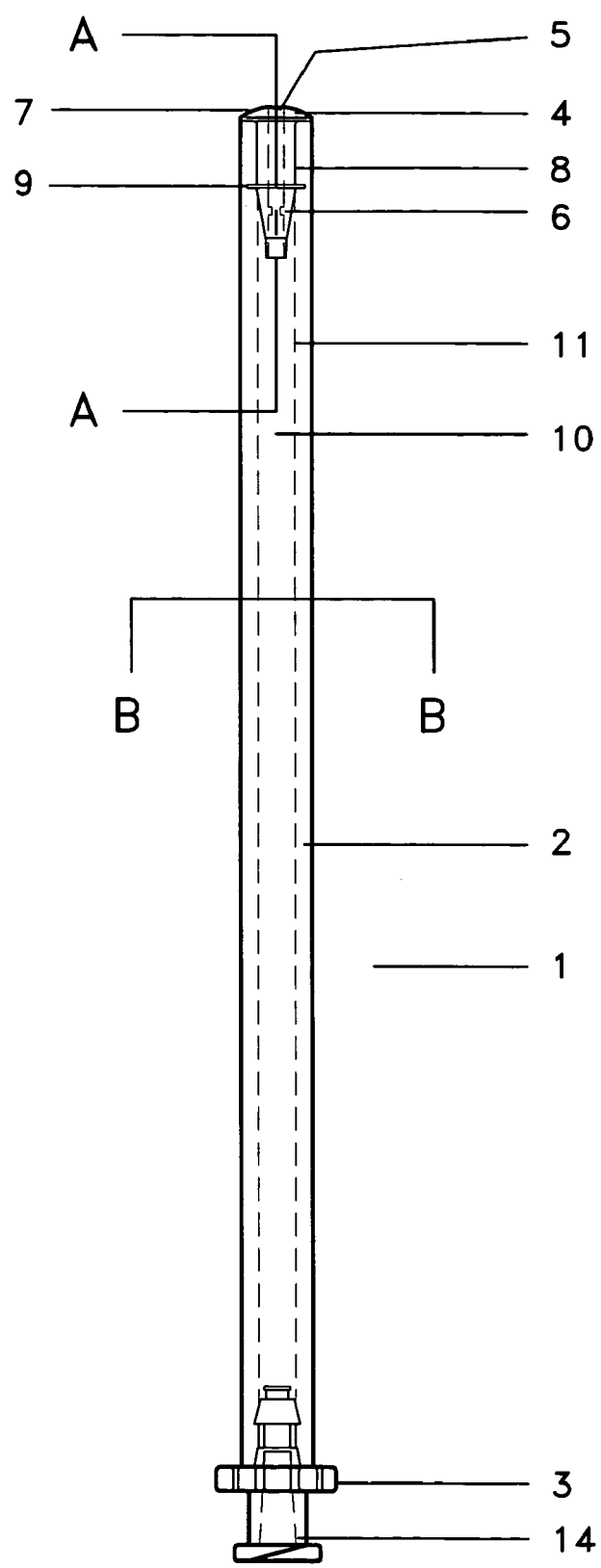
FIG. 1 is a drawing showing an elevation of a particular embodiment of the invention.

Specifically, the invention addresses apparatus and methods for the intranasal delivery of various compositions to equids. The basic technology may, however, have various applications in the medical or veterinary fields, for example, the invention may address the difficulties of delivering various compositions, including prophylactics or therapeutics, to a variety of targets susceptible to such variety of compositions in both humans and animals. The invention also provides both apparatus and methods for the effective delivery of a wide variety of compositions which may have application in numerous other settings, including commercial production facilities, research laboratories, medical or veterinary practices, or by individual consumers.

As can be easily understood, the basic concepts of the present invention may be embodied in a variety of ways. The invention involves both methods as well as apparatus to accomplish the appropriate methods. In this application, the methods are disclosed as part of the results shown to be achieved by the various apparatus described, and as steps which are inherent to utilization. They are simply the natural result of utilizing the apparatus or devices as intended or described. In addition, while some particular embodiments of the invention are disclosed to accomplish certain methods described, it would be understood that these can be varied in a number of ways. Importantly, as to all of the foregoing, all of these facets should be understood to be encompassed by this disclosure.

The components which make up the intranasal delivery system invention are first described. FIGS. 1 through 8 show a particular embodiment of the intranasal delivery system invention and is but one example of the delivery system invention as described. A dose administrator (1) assists the delivery of a "dose" to a desired "target". A dose may be any desired amount of a composition or desired amount of a combination of compositions. A dose does not necessarily have to be a medicament or be used to treat humans or animals. However, a dose may include prophylactic compositions such as vaccines or therapeutic compositions such as drugs or other compositions which are of research or medicinal interest such as proteins, nucleic acids, immunogens, live or inactivated viruses, reassortant live viruses, cold-adapted live viruses, attenuated live viruses, adjuvants, or may be other substances which are useful for the delivery of or effectiveness of such compositions. The dose may also be species specific compositions such as cold-adapted live equine influenza viruses which replicate only within a certain temperature range (such as from about 26° C. to about 30° C. in embryonated chicken eggs), or an cold-adapted live equine influenza virus which does not form plaques in tissue culture cells at a temperature above a certain range (such as above about 37° C. or above about 39° C.), or an cold-adapted live equine virus having a phenotype wherein protein synthesis is inhibited above about 39° C., or an equine cold-adapted live virus having a dominant interference phenotype, as examples in the equine field. More specifically, the dose may be particular strains of virus, such as those disclosed by U.S. patent application Ser. No. 09/133,921, hereby incorporated by reference, including equine influenza cold-adapted live viruses derived from strain A/equine/Kentucky/1/91 (H3N8); or EIV-P821 (identified by accession No. ATCC VR 2625), EIV-P824 (identified by accession No. ATCC VR 2624), MSV+5 (identified by accession No. 2627); or any progeny of any of said equine influenza viruses identified by such accession Nos.; or any EIV having the identifying characteristics of such ATCC VR strains.

Figure 9:
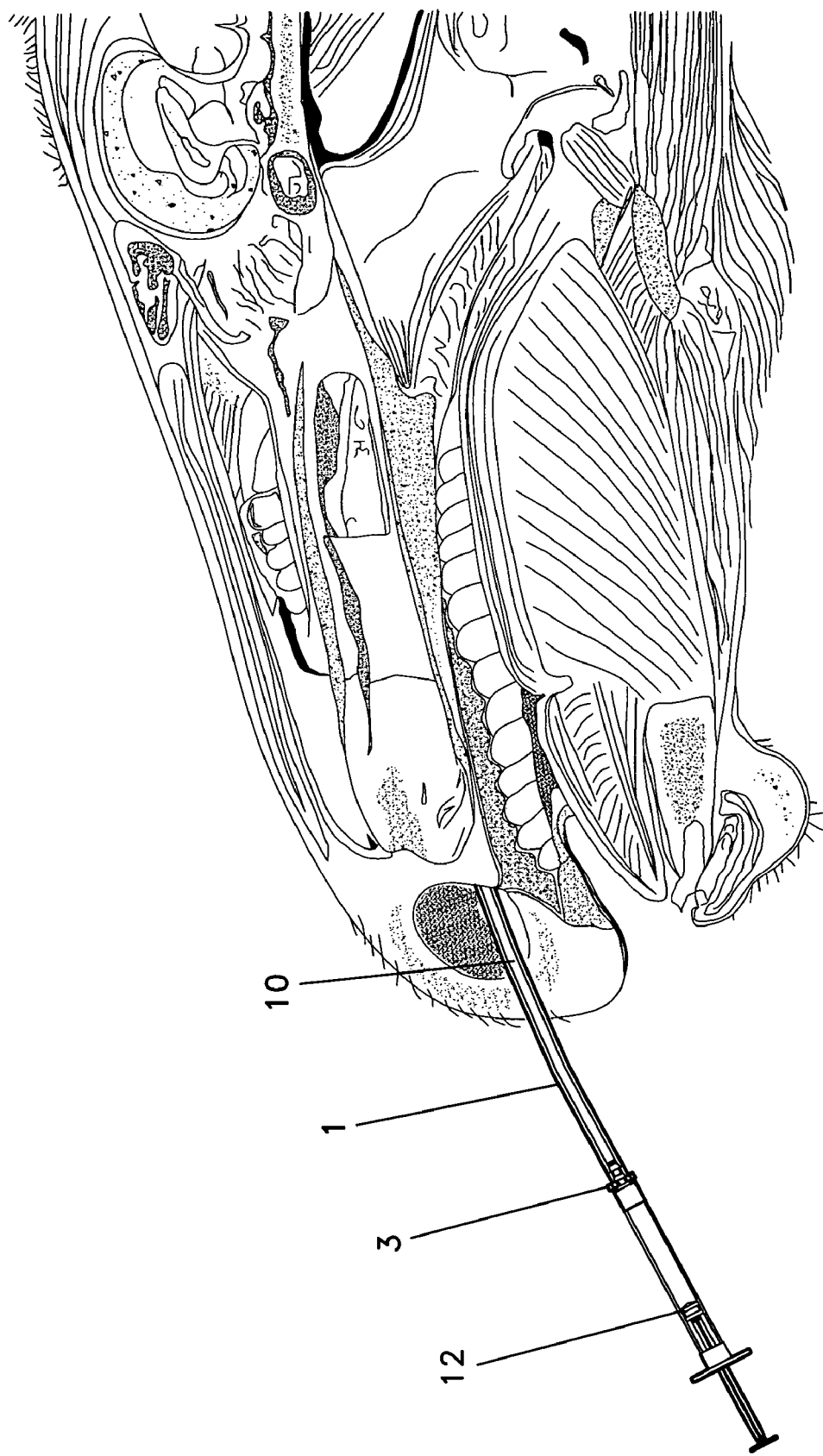
FIG. 9 is a drawing showing a particular embodiment of the invention being positioned within the nostril of an equid.
Figure 10:
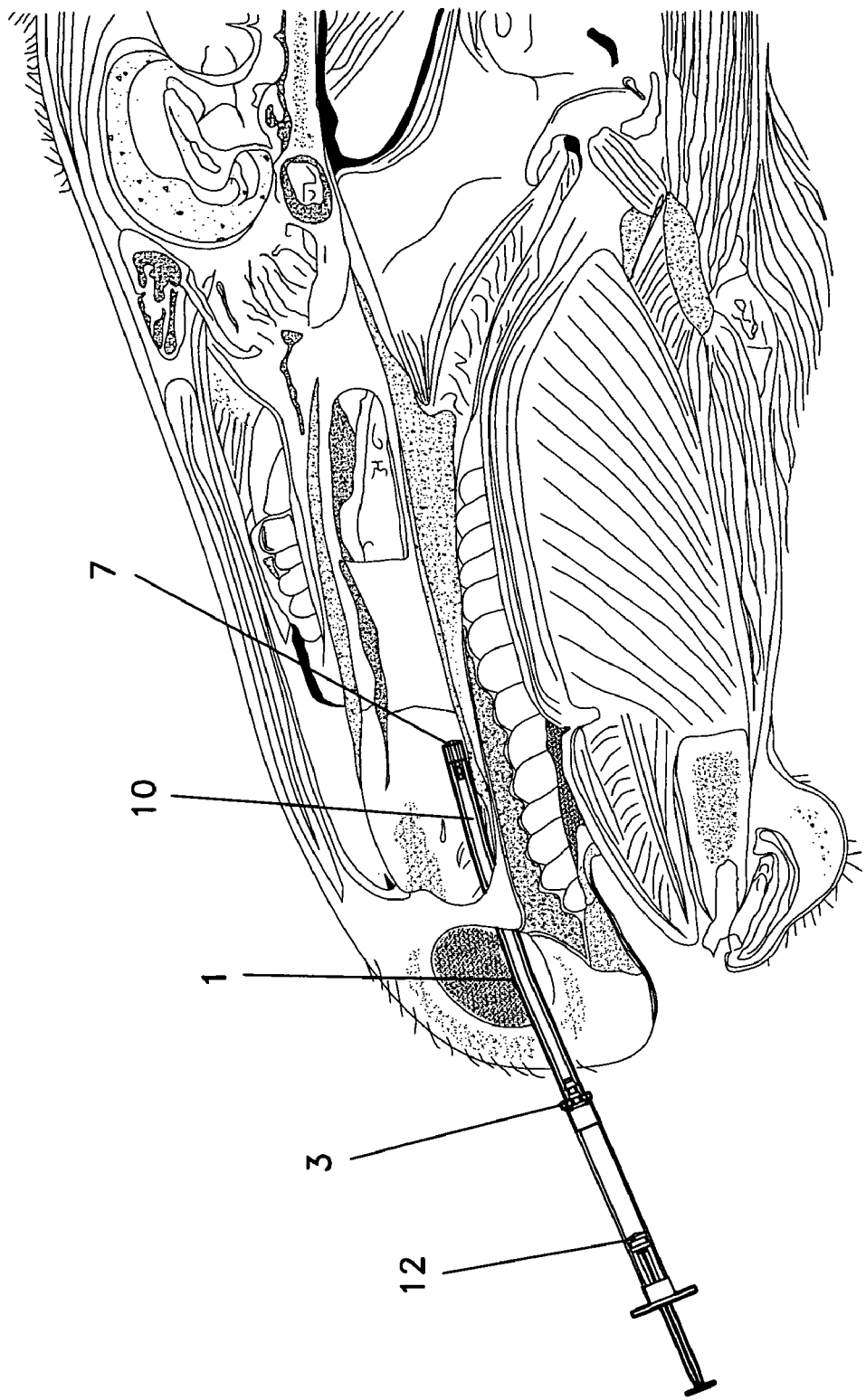
FIG. 10 is a drawing showing a particular embodiment of the invention being positioned within the nasal passage of an equid.
Figure 11:
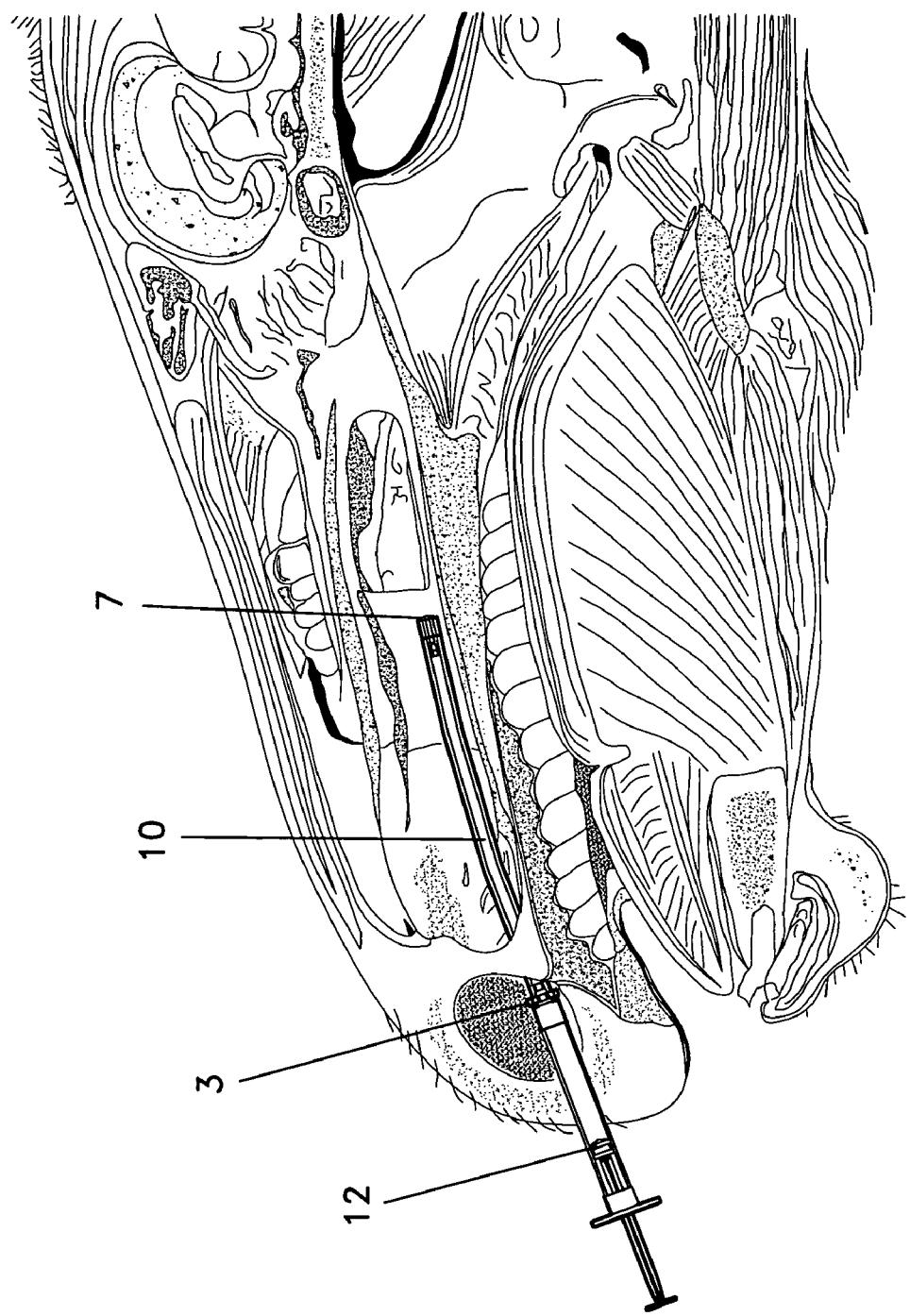
FIG. 11 is a drawing showing a particular embodiment of the invention positioned within the nasal passage of an equid by comparing the location of a dose-location coordinate element with an external portion of the nostril.

In general, a target to which the dose is delivered may include any desired location on any substrate. It may also include locations of anatomical designation both external or internal with respect to both humans and animals. The target may include gross anatomical features such as the mouth, eyes, ears, nose, genitals, or rectum, for example, or the target may be specific systems such as the central nervous system, the circulatory system or respiratory system, or the target may also include specific organs, tissues, cells, or other molecular structures associated with such gross anatomical features, systems, specific organs, tissues or cells. Specifically, as shown in FIGS. 9, 10, and 11, the target may be the nasal mucosa of the upper respiratory tract of an equid. Additionally, the target may be a location having specific attributes, such as a specific temperature, which makes the composition upon delivery more effective. For example, such specific temperature or other attributes may be important in promoting the replication of certain cold-adapted live viruses or other attribute-adapted viruses.

The dose administrator (1) may be a flexible material or a substantially rigid material depending on the application or anatomical characteristics of the species which it is designed to be used with. For example, a substantially rigid material may be selected for use with humans or bovine which may have a relatively short and uncomplicated intranasal passages to traverse in order to deliver the dose to the target or dose-location coordinate. Alternately, a more flexible dose administrator may be selected for use with equids which have longer intranasal passages to transverse and which may also have a blind-ending nasal passage (such as a nasal diverticulum) which may have to be worked around to deliver a dose to the desired target or dose location-coordinate.

The exterior configuration of the dose administrator may vary substantially in shape for delivery of compositions from application to application and may include, for example, cylindrical or conical configurations. As shown in FIG. 1, a dose administrator may have a substantially uniform cylindrical exterior. The length of the dose administrator may vary depending on the location of the target. For applications with equids which have longer nasal passages a cylindrical exterior surface having a radius in the range of about 1.5 millimeters (about 1/16 inch) to about 10 millimeters (about 0.4 inches), and a longitudinal length in the range of about 76 millimeters (about 3 inches) to about 180 millimeters (about 7 inches) may be appropriate. One particular embodiment of the flexible dose administrator shown by FIG. 1 has a cylindrical exterior surface of about 6.5 millimeters (about 0.25 inches) and a longitudinal length of about 150 millimeters (about 5.9 inches).

The material from which the dose administrator is made may also be compatible with the composition which the dose administrator will deliver such that the dose administrator may not be degraded or so that the composition of the dose may not be altered as, for example, by heat, light, ultraviolet radiation and the like. A material suitable for the intranasal delivery of many of the above mentioned doses may be glass, polyethylene, polypropylene, polyurethane, or polyvinyl chloride.

An axial collapse prevention element (2) may be coupled to the dose administrator. The axial collapse prevention element prevents excessive axial deflection of flexible dose administrators. Excessive axial deflection may prevent the dose administrator from being properly oriented in relation to the target. The axial collapse prevention element may comprise annular or longitudinal projecting surface(s) or a pattern formed on the exterior or interior surface of the dose administrator which provides additional axial resiliency, or may comprise fibers or strands of flexibly resilient material embedded in the material from which the dose administrator is made, or may be a flexibly resilient layer responsive to the exterior cylindrical surface of the dose administrator as shown in FIG. 1, although more than one layer may be used in some applications or with some types of doses. Specifically for applications with equids, a flexibly resilient layer of polyvinyl chloride or polyurethane, which may be a medical grade, having a thickness of about 1.5 millimeters (about 1/16 inch) may be used. The axial collapse prevention element (2) and the dose administrator (1) may have a unitized construction as shown in FIG. 1.

To assure that the dose is delivered to the desired target a dose-location coordinate indicator (3) may be coupled to the exterior of the dose administrator. The dose-location coordinate indicator may be a visually enhanced surface such as a mark, an annular projection as shown in FIG. 1, or any other element which permits location identification. The dose-location coordinate indicator may be positioned on the dose administrator such that when aligned with a particular stop element or anatomical feature the user may be assured that the dose is coordinated for subsequent delivery with a location which has a target susceptible to the dose (dose-location coordinate). This feature may be particularly useful when the dose administer is used to deliver a dose to a location that cannot be viewed directly. With respect to doses which are attribute or temperature sensitive the dose-location coordinate indicator may be positioned such that a dose-location coordinate has that particular attribute or temperature associated with it. For example, a dose-location coordinate indicator positioned to assure that a dose is delivered to the corresponding dose-location coordinate in the upper respiratory system of an equid having a temperature of between about 26° C. to about 34° C. may be essential to a virus cold-adapted to this temperature range. Specifically, with regard to particular equine applications involving the delivery of cold-adapted equine influenza virus the position of the dose-location coordinate indicator may be located at about 127 millimeters (five inches) to about 152 millimeters (six inches) from the delivery end or first end of the flexible dose administrator. This position can assure that the dose (such as a cold-adapted equine influenza virus) is delivered to a dose-location coordinate having a temperature at which replication can occur (about 26° C. to about 34° C.) and having mucosal cells which are susceptible to the dose. Naturally, for each application the dose-location coordinate should be affirmatively determined and the dose-location coordinate indicator positioned accordingly. The dose-location coordinate indicator and the dose administrator may also be of unitized construction.

Figure 2:
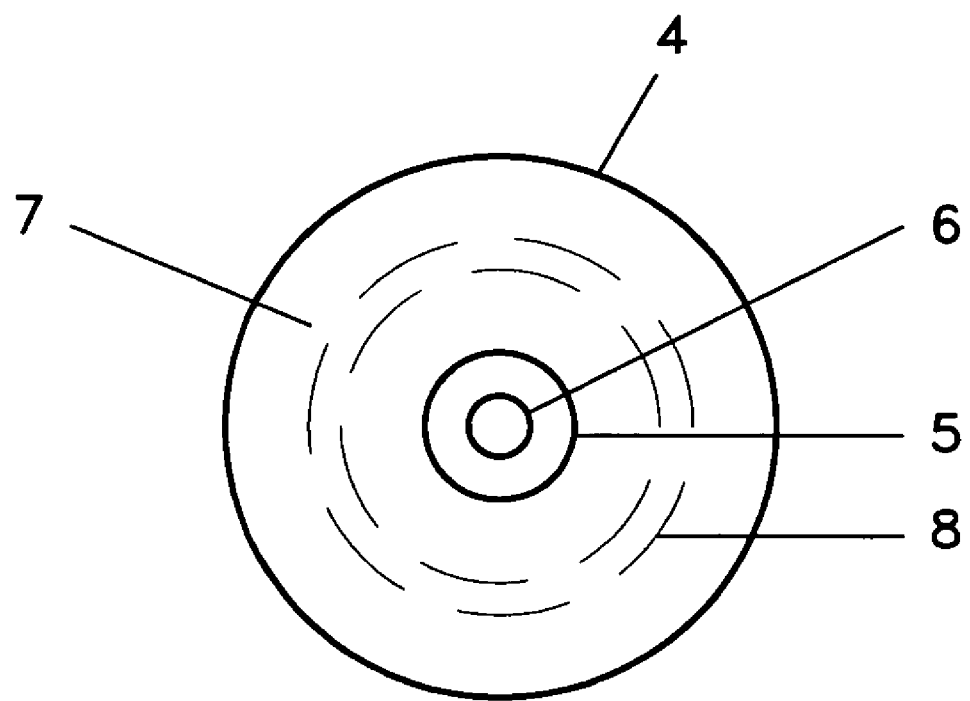
FIG. 2 is a drawing showing a top view of a particular embodiment of the invention.
Figure 3:
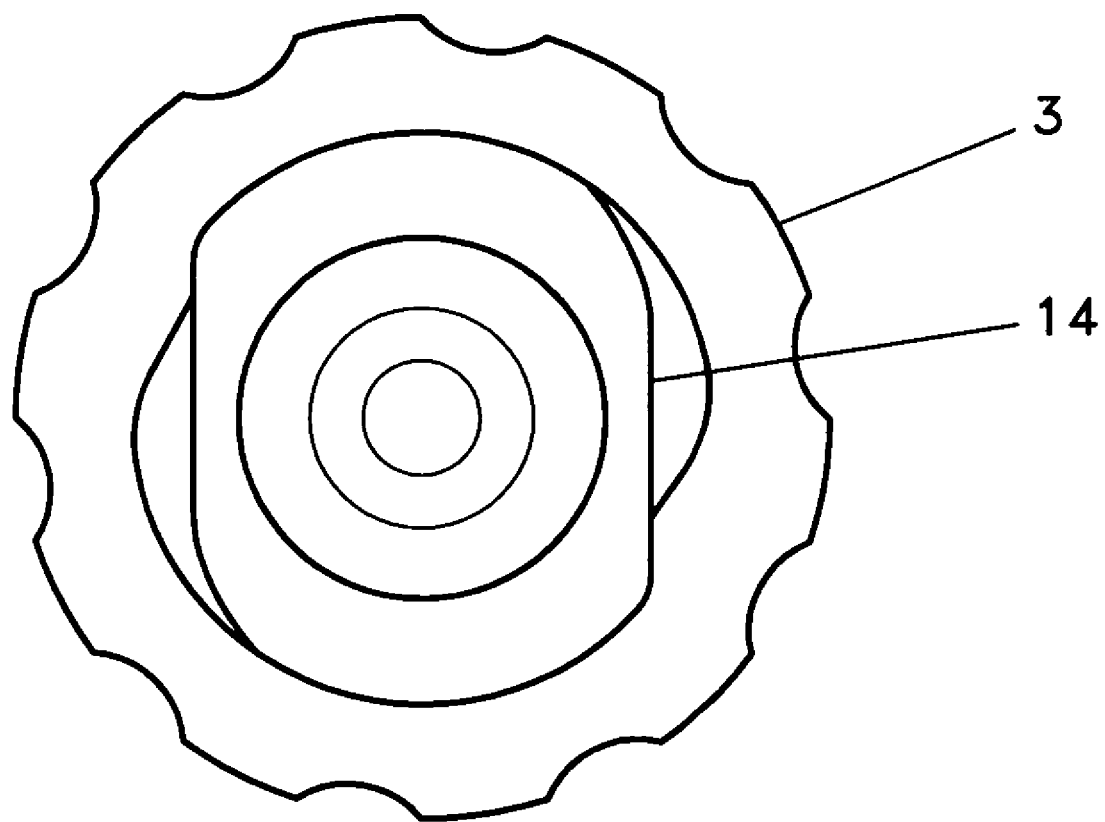
FIG. 3 is a drawing showing a bottom view of a particular embodiment of the invention.
Figure 4:
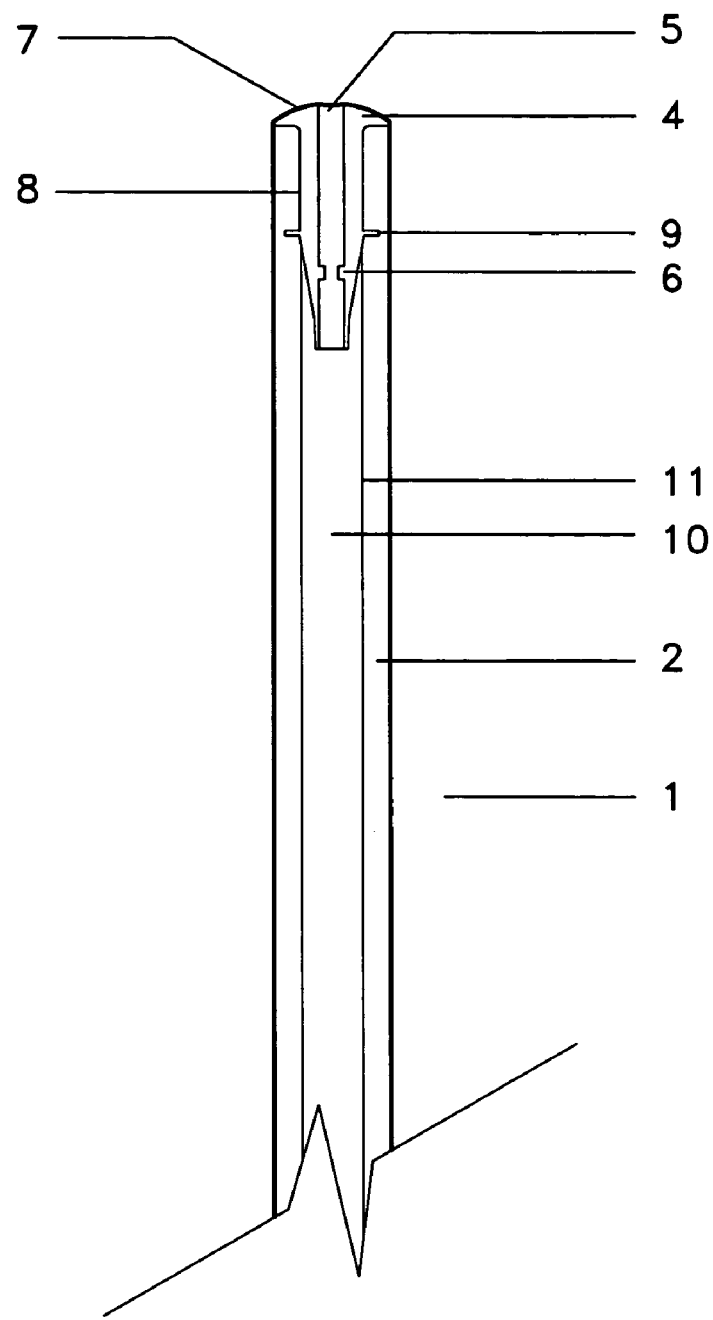
FIG. 4 is a drawing showing a cross section of a particular embodiment of an intranasal probe and dose administrator.
Figure 5:
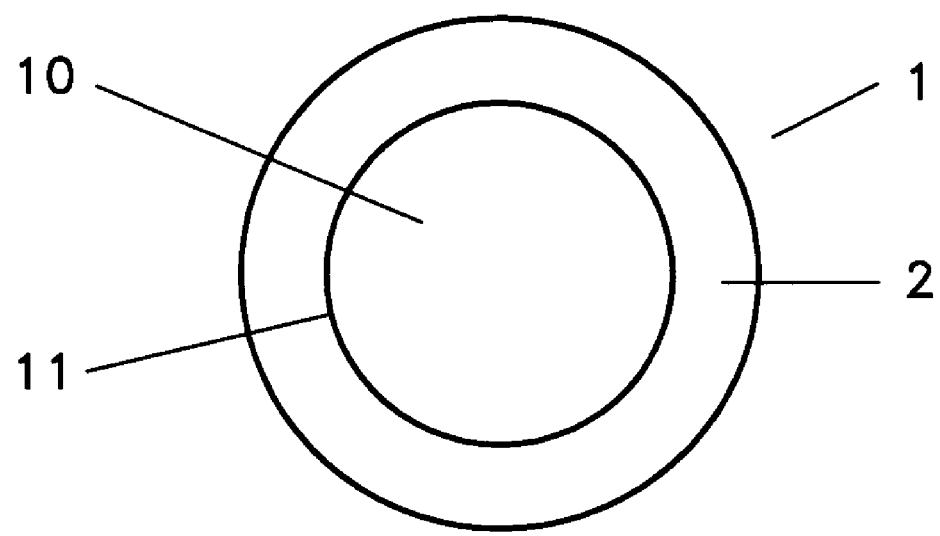
FIG. 5 is a drawing showing a cross section of a particular embodiment of a dose administrator having a conformable dose sequestration element.
Figure 6:
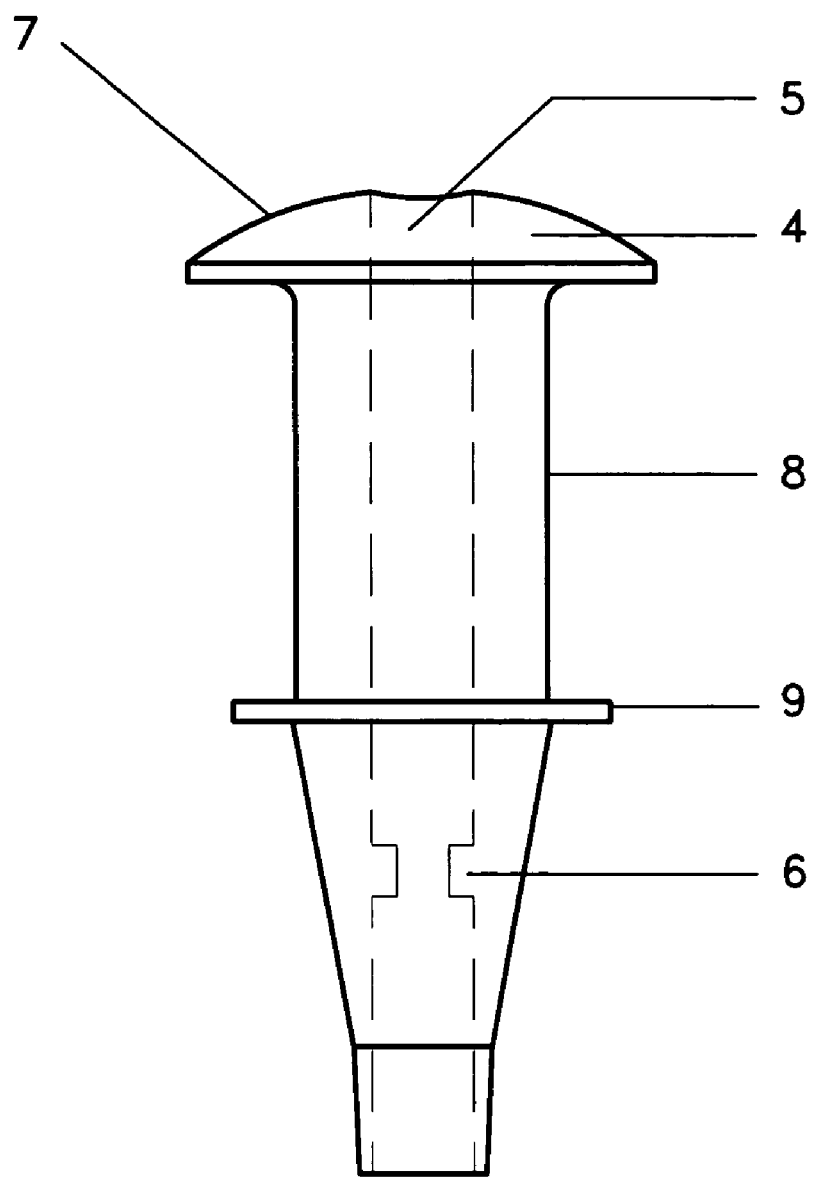
FIG. 6 is a drawing showing an elevation of a particular embodiment of a unitized construct having an intranasal probe, a force dissemination contact surface, a dose delivery aperture element, a stream delivery element, and an intranasal probe coupler.

An intranasal probe (4) may be responsive to a first end of the dose administrator. The intranasal probe can provide a surface on which a variety of dose delivery aperture elements, force dissemination contact surfaces, or an intranasal probe coupler may be attached. The dose delivery aperture element (5) may be a separate component having an aperture which penetrates the dose delivery aperture element. In that case, the dose delivery aperture element can be coupled to the intranasal probe which holds the aperture adjacent to the dose delivery administrator. Alternately the intranasal probe and the dose delivery aperture may be unitized. The aperture which penetrates the dose delivery aperture element may be further fitted with components which regulate the pressure, particle size, or the rate of delivery of the dose. A stream delivery element (6) may be coupled to the aperture, as shown in FIG. 2, 4 or 6, to prevent the dose from being delivered as discrete particles but rather delivered as substantially continuous concentered stream. The stream may be delivered with a pressure sufficient to propel the dose to the proper dose-location coordinate. Alternately, the aperture may be fitted with other elements which deliver the dose as a fine mist, course spray, or for topical application. For equine intranasal use, the stream delivery element (6) may have an orifice of about 0.75 millimeters (about 0.030 inches).

A force dissemination contact surface (7) having hebetated termini may be coupled to the intranasal probe as shown in FIG. 1, 2, 4, or 6. A purpose of the force dissemination surface may be to spread the forces from incidental contact of the dose administrator with other surfaces as the dose administrator is moved into position to deliver the dose to the proper dose-location coordinate. Spreading such forces from incidental contact may be important to prevent damage or injury to these surfaces. With respect to movement of the dose administrator into and out of anatomical passages, such as the intranasal passages, the force dissemination contact surface may prevent cutting, scoring or abrading of the tissue and minimize physical stimulation. For equine intranasal applications, a sphere cap having a radius of about 3 millimeters (about 0.125 inches) and a sphere cap height of about 1 millimeter (about 0.04 inches) may be used alone or in conjunction with a dose administrator having a cylindrical exterior surface with a radius of about 3 millimeters (about 0.125 inches) such that the force dissemination contact surface and the cylindrical exterior surface are contiguous.

An intranasal probe coupler (8) may be affixed to the intranasal probe (4). The first end of the intranasal probe coupler is responsive to the intranasal probe (4) while the second end is responsive to the dose administrator (1). At least one aperture communicates with the interior of the dose administrator and the dose delivery aperture element. The second end of the intranasal probe coupler may be responsive to either the exterior surface or the interior surface of the intranasal probe. As shown in FIG. 1, 4, or 6, the second end may comprise an annular barb (9) engaged to the interior cylindrical surface of the flexible dose administrator.

The intranasal probe (4), the intranasal probe coupler (8), the force dissemination surface (7), the dose delivery aperture (5), and the stream delivery element (6) may be unitized as a single component, as shown by FIG. 6, or unitized in combination with the dose administrator (1) or may be unitized in various combinations and permutations depending on the particular application.

Figure 7:
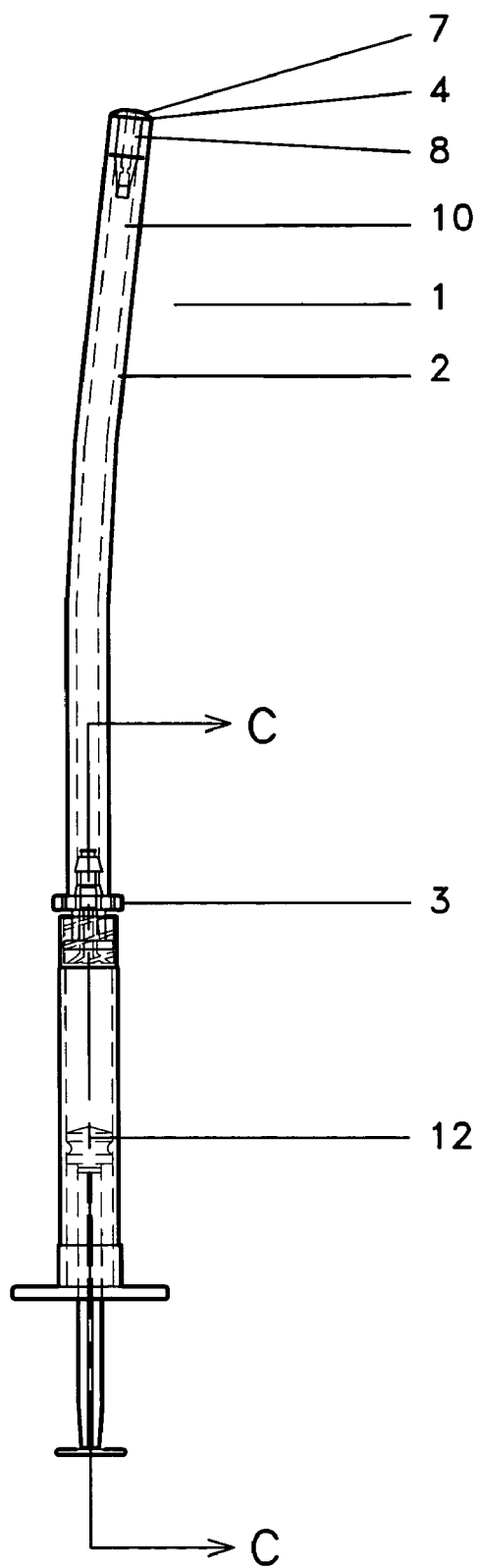
FIG. 7 shows an elevation of a particular embodiment of the delivery system.
Figure 8:
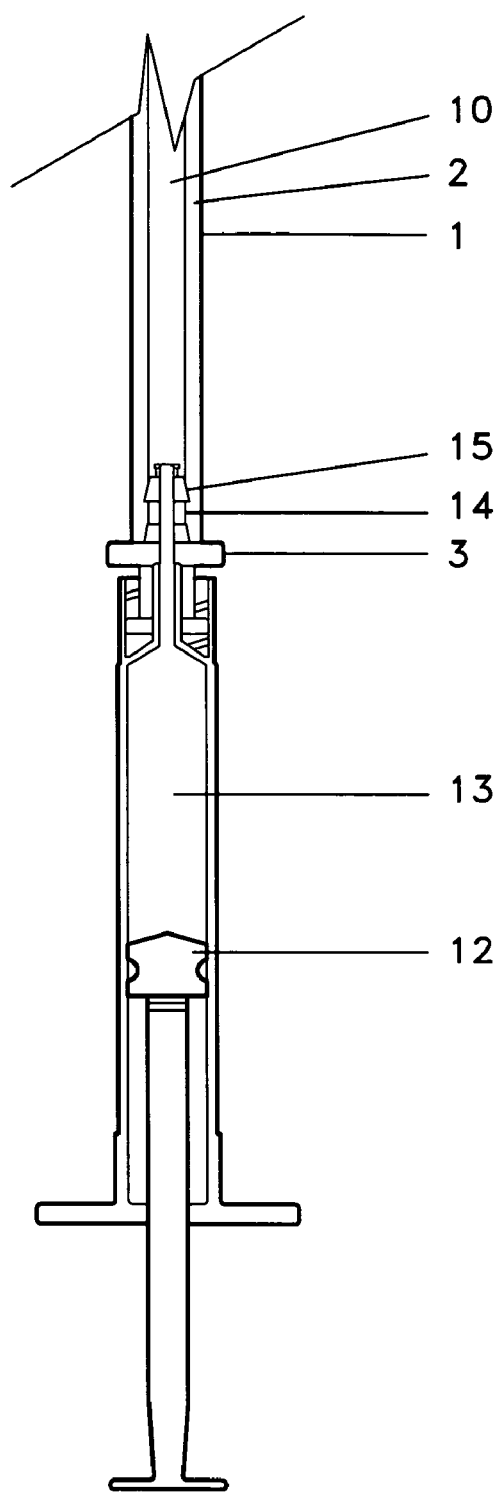
FIG. 8 is a drawing showing a cross section of a particular embodiment of the fluid dose propellent coupler and a particular embodiment of a force application element.

A conformable dose sequestration element (10) may communicate with the dose delivery aperture (5). The conformable dose sequestration element may provide a dose sequestration volume sufficiently large to contain or sequester at least one of the above-mentioned doses, either dry or combined with a diluent, such that the dose may be held separate from other components of the delivery system. The dose sequestration volume may also conform to any shape which may be desirable and may be located within the dose administrator as shown by FIG. 1, 4, or 7. With respect to some applications, the conformable dose sequestration element may comprise a penetrable membrane which separates the dose from the remaining volume of the dose administrator. The conformable dose sequestration element may also be configured without a penetrable membrane. In that case the dose sequestration volume may communicate with other components of the delivery system through at least one aperture. As shown by FIG. 1, the conformable dose sequestration element (10) may comprise a portion or all of the interior volume of the flexible dose administrator (1). It may be understood that the exterior surface of or the interior volume of the dose administrator may not be of uniform configuration (FIG. 1 shows a generally uniform cylindrical configuration). The dose sequestration element may conform to any portion or all of such non-uniform configuration of the dose administrator. Alternately, the dose sequestration element may be a separate component made responsive to the dose delivery aperture during delivery of the dose to the dose-location coordinate.

The conformable dose sequestration element may also feature a dose retainer (11) located proximate to the dose delivery aperture (5) so as to retain the dose within the dose sequestration volume proximate to the dose delivery aperture. For some applications, this may comprise a penetrable membrane. In other applications, the conformable dose sequestration element may be configured to hold the dose adjacent to the dose delivery aperture. As shown by FIG. 1, 4, or 7, the conformable dose sequestration element may be configured as a capillary which may hold the dose combined with a diluent proximate or adjacent to the dose delivery aperture in part or in whole by capillary forces. Such a capillary may be about 3 millimeters (about ⅛ inch) as shown in FIG. 1. The capillary, as can be understood, may be smaller or larger as the application requires.

As such, the conformable dose sequestration element (10), the dose retainer (11), the dose administrator (1), and the axial collapse prevention element may have unitized construction or may be unitized in various combinations or permutations as certain applications require.

The conformable dose sequestration element (10) sequestering the dose may be separated from a force application element (12) with a volume of fluid dose propellent (13). The fluid dose propellent may be a gas such as air or may be liquid such as water or a saline solution or may contain other compositions which enhance either the dose or the delivery of the dose. The fluid dose propellent may have a volume which is equal to or greater than the dead volume of the dose delivery system. This amount of fluid dose propellent may be at least the minimum volume which will deliver the entire dose when acted upon by the force application element (minimum dose delivery volume). The volume of fluid dose propellent may have a volume greater than the minimum dose delivery volume. Such volume greater than the minimum dose delivery volume, when acted upon by the force application element, can expel the dose from the dose administrator or conformable dose sequestration element and then chase the dose with the remaining portion of fluid dose propellent which exceeds the minimum dose delivery volume. Chasing the dose with the remaining portion of the fluid dose propellent can assure that substantially the entire dose may be delivered to the dose-location coordinate. As shown by FIG. 1, the minimum delivery volume may about 1 to about 1.5 milliliters which may be chased with a remaining portion of fluid dose propellent as desired.

A fluid dose propellent coupler (14) may be used to couple the dose administrator (1) to the force application element (12). As shown in FIG. 1, 7, or 8, the first end of the fluid dose propellent coupler may comprise an annular barb (15) responsive to the interior surface of a flexible dose administrator. The second end of the fluid dose propellent coupler may comprise a syringe adaptor. The syringe adaptor may be a leur-lock to positively lock a syringe or other force application element to the dose administrator. As shown in FIG. 1 or 8, the fluid dose propellent coupler (14) and the dose-location coordinate indicator (3) may have unitized construction.

The force application element (12) may be responsive to the second end of the dose administrator (1) or may be coupled to the fluid dose propellent coupler (14) as above mentioned. The force application element may be any component or substance which provides sufficient force to expel the dose from the dose administrator (1) or the conformable dose sequestration element (10) to the dose-location coordinate. As shown in FIG. 7 or 8, the force application element may be a plunger type syringe which could be of any size which the user finds practical or the application requires. Alternately, the force application element may be a mechanical bellows, a squeeze type bottle, compressed gas, a liquid under pressure or otherwise as would be readily understood by those with skill in the dose delivery field.

The force application element (12) may have unitized construction with the dose administrator (1), the intranasal probe (4), the conformable dose sequestration element (10), the force dissemination contact surface (7), the dose delivery aperture (5), the stream delivery aperture (6), the axial collapse prevention element (2), or the dose-location coordinate element (3), or any of these elements in certain combinations or permutations.

An intranasal delivery system as described above may be produced by first providing a dose delivery aperture element (5) and providing a stream delivery element (6) if stream delivery of the dose to the target is desirable. If so the stream delivery aperture can be affixed to the dose delivery aperture. The next step involves coupling an intranasal probe (4) to the dose delivery aperture and thereafter coupling a force dissemination contact surface (7) having hebetated termini to the intranasal probe. Coupling an intranasal probe coupler (8) to the intranasal probe may be required for joining the dose administrator. Assembly of these parts may be accomplished with standard fasteners, with mated surfaces, by bonding with a solvent, by friction fit, or otherwise. Naturally, these steps may be incorporated into unitized construction as shown in FIG. 6 and may not comprise additional discrete steps of assembly. Joining the dose administrator (1) can comprise engaging the interior of dose administrator (1) with the intranasal probe coupler (8) which may have an annular barb (9) to secure the dose administrator to the intranasal probe. Alternately the intranasal probe may be secured to the exterior surface of the dose administrator with mated surfaces such as threads, by friction fit or by bonding the surfaces together with a solvent. The configuration of the conformable dose sequestration element (10) can be selected to have a volume which will sequester at least one dose and is compatible with the configuration of the dose administrator. The conformable dose sequestration element (10) can be coupled to the dose administrator (1) if it is not of unitary construction with the dose administrator as shown by FIG. 1. Joining the axial collapse prevention element to the dose administrator (2) may comprise the bonding of discrete components annularly or longitudinally to the dose administrator but these steps may be accomplished in the design of a unitary construct comprising the dose administrator (1), conformable dose sequestration element (10), and the axial collapse prevention element (2) thereby eliminating additional discrete production steps. Positioning of the dose-location coordinate indicator (3) at a location on the dose administrator may comprise molding a visually enhanced surface onto the dose administrator or the fluid dose propellent coupler such as a mark, a projecting surface, a recessed surface, or an annular projection as part of a unitized construct similar to that shown in FIG. 1, 3, 7, or 8. Alternately, it may comprise affixing such visually enhanced surfaces, or adhesive backed label, or printed graphic to the proper location on the exterior surface of the dose administrator or the fluid dose propellent coupler as a discrete assembly step. The dose administrator (1) may be joined directly to the force application element (12) by slip fit, friction fit, or by mated surfaces such as threads or leur-lock or other engaging or locking devices. Alternately as shown by FIG. 1, 3, 7, or 8 the dose administrator (1) and the force application element (12) may be joined by a dose propellent coupler which has a first end configured to engage either the interior or exterior surface of the dose administrator.

The dose delivery system as described above may be used to deliver a variety of compositions to both humans and animals including various doses intranasally. As shown by FIG. 9, 10, or 11, for example, the intranasal delivery system may be used to deliver such variety of compositions to equids, humans, or other animals intranasally. In one embodiment of the invention, a dose as described above may be first sequestered within a conformable dose sequestration element (10) which separates the dose from the force application element (12) with a volume of fluid dose propellent (13). The dose may be sequestered as a substantially dry composition within the conformable dose sequestration element (10) or may be a substantially dry composition in a separate container. Establishing at least one dose in a volume of diluent can be accomplished by either combining the diluent to the dry dose in the separate container or by submerging the dose delivery aperture (5) into the diluent and reducing the pressure within the conformable dose sequestration element (10) thereby transferring the diluent to the conformable dose sequestration element. Alternately, the dose combined with the diluent in the separate container may be drawn into the conformable dose sequestration element in a similar fashion. Retaining the dose adjacent to the dose delivery aperture with a dose retainer (11) or capillary forces may provide more consistent delivery of the dose to the dose-coordinate location. The above procedure may be accomplished after measuring a volume of fluid dose propellent in excess of the minimum dose delivery volume. After positioning the intranasal probe within a nostril of the human or animal, such as an equid as shown by FIG. 9, the intranasal probe is positioned by sliding the intranasal probe into the nasal passage. Positioning a dose-location coordinate indicator (3) into proximity with an exterior portion of the nostril can assure a dose-location coordinate having a target that is susceptible to the dose or can assure that the dose-location coordinate has a temperature of about 26 C. to about 34 C. or as might be appropriate for a particular cold-adapted virus. With respect to equids, guiding the intranasal probe so as to not enter the false nostril can be also assured by observing that the dose-location coordinate indicator is in proximity with the exterior portion of the nostril. Once the intranasal probe is properly positioned at the dose-location coordinate, terminating sliding of the intranasal probe up the nostril prepares the device for the step of propelling the dose from the conformable dose sequestration element. Propelling the dose from the dose sequestration volume of the conformable dose sequestration element may be accomplished by applying force to the fluid dose propellent which is responsive to the dose. A portion of the fluid dose propellent is used for propelling the dose and delivering the dose onto the target. Chasing the dose with a remaining portion of the fluid dose propellent volume assures that the entire dose has been propelled from the dose sequestration volume and delivered to the target. Streaming the dose onto the target may be more effective when it is desirable to minimize the creation of smaller particles of the dose which may remain suspended in the respiratory volume, or distributed away from the target, for example.

Kits may be produced, assembled or commercialized from the various above mentioned elements in various combinations or permutations. For example, a lyophilized cold-adapted equine influenza virus (perhaps of the various strains above-mentioned) in an ampule, a dose administrator, and a force application element may be packaged for sale as a kit which can be convenient for the consumer. A diluent in a separate ampule may be added in a more complete kit. The various elements of the equine intranasal delivery device, which could be any of the combinations or permutations as described above, could be added as supplements to the kit. Naturally, the dose could be quite specific, such as certain strains of cold-adapted equine influenza viruses, such as those above-mentioned, may be packaged for use with many types of dose administrators and force application elements. Conversely, the delivery device could be quite specific, such as for a particular type of equid, for use with various materials, compositions, or other medicaments. As such, many kits may incorporate aspects or embodiments of the invention even though all the aspects of the kit are not produced by the same manufacturer.

It is thought that the apparatuses and methods of the embodiments of the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element disclosed should be understood to encompass a disclosure of the action which that physical element facilitates.

Regarding this last aspect, and as but one example the disclosure of a "conformable dose sequestration element" should be understood to encompass disclosure of the act of "conforming a dose sequestration element"—whether explicitly discussed or not—and, conversely, were there only disclosure of the act of "conforming a dose sequestration element", such a disclosure should be understood to encompass disclosure of a "dose sequestration element". Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in any information disclosure filed with and/or for the application are hereby incorporated by reference, however, as to each of the above, to the extent that such information or statements incorporated by reference might be considered inconsistent with the patenting of this/these invention(s) such statements are expressly not to be considered as made by the applicant(s).

Further, the disclosure should be understood to include support for each feature, component, and step shown as separate and independent inventions as well as the various combinations and permutations of each.

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like. Such terms are intended to have an inclusive meaning rather than an exclusive one and should be interpreted in their most expansive form so as to afford the applicant the broadest coverage legally permissible. Therefore, in countries such as Australia and the like, such terms are not intended to have an exclusive, or more limited meaning.

Thus, the applicant(s) should be understood to claim at least: i) the delivery devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, and x) the various combinations and permutations of each of the elements disclosed.

We claim:

1. An equine intranasal dose delivery device, comprising:
a flexible tubular dose administrator having a length disposed between a first end and a second end and having an external surface configured to insert substantially the entirety of said length within a nasal passage of an equid animal;
b. at least one dose delivery aperture which allows fluidic communication between the interior and the exterior of said flexible dose administrator, said at least one dose delivery aperture having a location proximate said first end of said flexible tubular dose administrator; and
c. a stream delivery element coupled within said at least one dose delivery aperture, said stream delivery element having a structure configured to deliver an equine dose in a dose diluent substantially as a stream to avoid delivery of said equine dose as discrete particles to a target within said nasal passage of said equid animal.

2. An equine intranasal dose delivery device as described in claim 1, wherein said flexible tubular dose administrator has a length of between about 75 millimeters and about 180 millimeters.

3. An equine intranasal dose delivery device as described in claim 2, wherein said flexible tubular dose administrator has an external diameter of between about 2 millimeters and about 7 millimeters.

4. An equine intranasal dose delivery device as described in claim 3, wherein said flexible tubular dose administrator has a wall thickness of between about 0.3 millimeters and about 1.6 millimeters.

5. An equine intranasal dose delivery device as described in claim 4, wherein said tubular configuration has an internal diameter of between about 1.4 and about 4.0 millimeters.

6. An equine intranasal dose delivery device as described in claim 1, wherein said flexible tubular dose administrator has a length of between about 130 millimeters and about 160 millimeters.

7. An equine intranasal dose delivery device as described in claim 6, wherein said flexible tubular dose administrator has an external diameter of between about 6 millimeters and about 7 millimeters.

8. An equine intranasal dose delivery device as described in claim 7, wherein said flexible tubular dose administrator has a wall thickness of about 0.35 millimeters.

9. An equine intranasal dose delivery device as described in claim 8, wherein said tubular configuration has an internal diameter of about 1.8 millimeters.

10. An equine intranasal dose delivery device as described in claim 1, wherein said flexible tubular dose administrator has a length of about 155 millimeters.

11. An equine intranasal dose delivery device as described in claim 10, wherein said flexible tubular dose administrator has an external diameter of between about 2 millimeters and about 3 millimeters.

12. An equine intranasal dose delivery device as described in claim 11, wherein said flexible tubular dose administrator has a wall thickness of about 1.5 millimeter.

13. An equine intranasal dose delivery device as described in claim 12, wherein said tubular configuration has an internal diameter of about 3.3 millimeters.

14. An equine intranasal dose delivery device as described in claim 1, wherein said at least one dose delivery aperture comprises a plurality of dose delivery apertures.

15. An equine intranasal dose delivery device as described in claim 1, wherein said at least one dose delivery aperture comprises at least two dose delivery apertures.

16. An equine intranasal dose delivery device as described in claim 1, wherein said at least one dose delivery aperture comprises at least three dose delivery apertures.

17. An equine intranasal dose delivery device as described in claim 1, wherein said at least one dose delivery aperture comprises at least four dose delivery apertures.

18. An equine intranasal dose delivery device as described in claim 1, wherein said flexible tubular dose administrator and said at least one dose delivery aperture comprise a single piece flexible tubular dose administrator having said at least one dose delivery aperture proximate to said first end.

19. An equine intranasal dose delivery device as described in claim 1, further comprising an intranasal probe coupled to said flexible tubular dose administrator, wherein said at least one dose delivery aperture passes through said intranasal probe to provide communication between the interior and the exterior of said flexible tubular dose administrator.

20. An equine intranasal dose delivery device as described in claim 1, wherein said coupler and said flexible tubular dose administrator comprise a single piece flexible tubular dose administrator having said second end configured to engage a propellant source.

21. An equine intranasal dose delivery device as described in claim 20, wherein said coupler further comprises a luer configured to engage a syringe.

22. An equine intranasal dose delivery device as described in claim 21, wherein said luer further comprises a luer lock to fix position of said syringe relative to said luer.

23. An equine intranasal dose delivery device as described in claim 1, wherein said equine dose has a location in the interior of said flexible tubular dose administrator.

24. An equine intranasal dose delivery device as described in claim 1, wherein the interior of said flexible tubular dose administrator sequesters said equine dose.

25. An equine intranasal dose delivery device as described in claim 1, said equine dose comprises a material selected from the group consisting of: a substance, a composition, a therapeutic composition, a prophylactic composition, a drug, a protein, a nucleic acid, an immunogen, an immunogen which elicits an immune response, a live virus, a reassortant live virus, a cold-adapted live virus, an attenuated live virus, an equine cold-adapted live influenza virus which replicates in embryonated chicken eggs within a temperature range from about 26° C. to about 30° C., an equine influenza cold-adapted live virus which does not form plaques in tissue culture cells at a temperature above about 37° C., an equine influenza cold-adapted live virus which does not form plaques in tissue culture cells at a temperature above about 39° C., a equine cold-adapted live virus having a phenotype wherein protein synthesis is inhibited above about 39° C., an equine cold-adapted live virus having a dominant interference phenotype, an equine influenza cold-adapted live virus derived from strain A/equine/Kentucky/1/91 (H3N8), EIV-P821 (identified by accession No. ATCC VR 2625), EIV-P824 (identified by accession No. ATCC VR 2624), MSV+5 (identified by accession No. 2627), any progeny of any of said equine influenza viruses identified by such accession Nos., any EIV having the identifying characteristics of said ATCC VR strains, or an equine influenza cold adapted live virus having about $10^5$ $TCID_{50}$ to about $10^8$ $TCID_{50}$ units.

26. An equine intranasal dose delivery device as described in claim 1, wherein said tubular dose administrator has sufficient flexure to position said at least one aperture at a location within the nasal passage of an equid beyond the nasal diverticulum.

* * * * *